(12) United States Patent
Shaner et al.

(10) Patent No.: US 6,281,168 B1
(45) Date of Patent: Aug. 28, 2001

(54) HERBICIDAL COMPOSITIONS AND METHOD OF SAFENING HERBICIDES USING BENZOTHIAZOLE DERIVATIVES

(75) Inventors: Dale Lester Shaner, Lawrenceville, NJ (US); Helmut Siegfried Baltruschat, Schweppenhausen; Norbert Nelgen, Jugenheim, both of (DE)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/484,562

(22) Filed: Jan. 18, 2000

Related U.S. Application Data

(60) Provisional application No. 60/116,541, filed on Jan. 19, 1999.

(51) Int. Cl.$^7$ ................................................... A01N 25/32
(52) U.S. Cl. .......................................................... 504/106
(58) Field of Search ............................................. 504/106

(56) References Cited

U.S. PATENT DOCUMENTS

| | | | |
|---|---|---|---|
| 3,536,728 | 10/1970 | Yates et al. ........................... | 260/304 |
| 4,931,581 | 6/1990 | Schurter et al. ....................... | 560/18 |
| 5,169,951 | 12/1992 | Sutter et al. .......................... | 548/212 |
| 5,229,384 | 7/1993 | Kunz et al. ....................... | 514/234.2 |
| 5,304,652 | 4/1994 | Kunz et al. ........................... | 548/126 |
| 5,447,945 | 9/1995 | Sutter et al. .......................... | 514/373 |
| 5,945,451 | 2/2000 | Ruess et al. .......................... | 514/361 |
| 6,031,153 | 2/2000 | Ryals et al. ........................... | 800/279 |

FOREIGN PATENT DOCUMENTS 0 039 795 B1   12/1983   (DE) .

OTHER PUBLICATIONS

Salicylsaure und BTH sind Gegenspieler von Oxyfluorfen in Zellsuspensionskulturen der Sojabohne (Glycine max) 1998.

Primary Examiner—S. Mark Clardy
(74) Attorney, Agent, or Firm—Barbara V. Maurer

(57) ABSTRACT

The invention relates to methods for protecting cereal crops from injury caused by a herbicidally effective amount of a herbicide, in particular, herbicides selected from the group consisting of AHAS-inhibiting, ACCase-inhibiting and HPPD-inhibiting herbicides, which comprises applying to the crop plant, the seed of the crop, or the soil surrounding the crop or crop seed an effective non-phytotoxic antidotal amount of a benzothiazole derivative of formula I

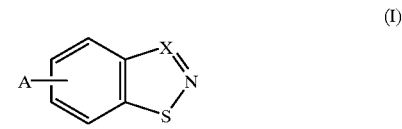

(I)

wherein

A represents an alkyl, alkoxy, haloalkoxy, hydroxy, cyano or nitro group or a group of the formula

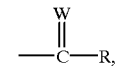

in which W represents O or S, and R represents a hydroxy, thiol, alkoxy, thioalkyl, amino, alkylamino or dialkylamino group; and X represents CH or N;

Also included are safened herbicidal compositions comprising a herbicidally effective amount of a herbicide and an effective nonphytotoxic antidotal amount a benzothiazole derivative of formula I.

21 Claims, No Drawings

HERBICIDAL COMPOSITIONS AND METHOD OF SAFENING HERBICIDES USING BENZOTHIAZOLE DERIVATIVES

This application claims priority from copending provisional application(s) Ser. No. 60/116,541 filed on Jan. 19, 1999.

BACKGROUND OF THE INVENTION

One of the most common practices for controlling undesirable plant species is the use of post-emergent selective herbicides. For example, certain compounds which inhibit the enzymes acetohydroxyacid synthase (AHAS), acetyl CoA carboxylase (ACC) and/or 5-hydroxyphenyl-pyruvate-dioxygenase (HPPD) are known herbicides which are effective against certain annual and perennial grass and broadleaf weeds. Unfortunately these herbicides cannot be used in all crops, especially cereal crops such as corn, wheat, barley and rice, because of unacceptable crop tolerance.

Therefore what is needed in the art is a herbicide which is effective against weeds, while protecting the gramineous crop from injury.

It is known, for example from U.S. Pat. No. 4,931,581 and U.S. Pat. No. 5,229,384, that certain benzothiadiazole derivatives have the capability to prevent healthy plants from attack by harmful microorganisms by stimulating the plants' own biological defense system. The term for the plant response on such stimulating agents is systemic acquired resistance (SAR).

SUMMARY OF THE INVENTION

The present invention relates to a a method for protecting cereal crops from injury caused by a herbicidally effective amount of a herbicide, in particular, selected from the group consisting of AHAS-inhibiting, ACCase-inhibiting and HPPD-inhibiting herbicides, which comprises applying to the crop plant, the seed of the crop, or the soil surrounding the crop or crop seed an effective non-phytotoxic antidotal amount of a benzothiazole derivative of formula I

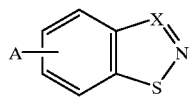

(I)

wherein

A represents an alkyl, alkoxy, haloalkoxy, hydroxy, cyano or nitro group or a group of the formula

in which

W represents O or S, and

R represents a hydroxy, thiol, alkoxy, thioalkyl, amino, alkylamino or dialkylamino group; and X represents CH or N.

This invention also includes a safened herbicidal composition which is effective against weeds, but spares the crop.

The invention furthermore relates to seeds treated with an effective nonphytotoxic antidotal amount a benzothiazole derivative of formula I.

Other objects and advantages of the present invention will be apparent to those skilled in the art from the following description and the appended claims.

DETAILED DESCRIPTION OF THE PREFERRED EMBODIMENTS

The invention relates to a method for protecting cereal crops from injury caused by a herbicidally effective amount of herbicides which comprises applying to the crop plant, the seed of the crop, or to the soil surrounding the crop or crop seed an effective non-phytotoxic antidotal amount of a benzothiazole derivative of formula I.

Benzothiazole derivatives which are suitable for use in the present invention are the compounds of formula I. Of these, preferred benzothiazole derivatives are the compounds of formula I wherein X represents N, and A is a —CO—SCH$_3$ group attached to the 7-position of the benzothiazole moiety or a methyl, cyano, hydroxy or difluoromethoxy group attached to the 4-, 5- or 6-position of the benzothiazole moiety.

The benzothiadiazole derivatives of formula I wherein A$^1$ represents a methyl, hydroxy, or a C$_{1-6}$ fluoroalkoxy group, are especially preferred for safening seeds, especially barley seeds.

As used herein, "Halogen" means a fluorine, chlorine, bromine or iodine atom, and preferably is fluorine, chlorine or bromine.

Generally, when any of the above mentioned moieties comprises an alkyl or alkoxy group, such groups, unless otherwise specified, may be linear or branched and may contain 1 to 6, and preferably 1 to 4, carbon atoms. Examples of such alkyl groups are methyl, ethyl, propyl, isopropyl and butyl. Representative alkoxy groups are those such as methoxy, ethoxy, propoxy, butoxy, and the corresponding branched chain analogs thereof.

Generally, when any of the above mentioned moieties comprises a haloalkoxy group, such groups, unless otherwise specified, may be linear or branched and may contain 1 to 6, and preferably 1 to 4, carbon atoms. Examples of such groups are halomethoxy, haloethoxy, halopropoxy, haloisopropoxy, halobutoxy, haloisobutoxy and halo-tertiary-butoxy groups. Haloalkoxy moieties of any groups within the definitions used herein can contain one or more halogen atoms, preferably fluorine, chlorine or bromine. Haloalkoxy preferably represents mono-, di-, tri- or perfluoroalkoxy groups, especially difluoromethoxy, trifluoromethoxy, pentafluoroethoxy, or 2,2,2-trifluoroethoxy, with difluoromethoxy being especially preferred.

The alkylamino groups are those wherein the alkyl portion contains 1 to 6, and preferably 1 to 4, carbon atoms, and are typically aminomethyl, 2-aminoethyl and the like. Dialkylamino substituents likewise contain 1 to 6, and preferably 1 to 4, carbon atoms in the alkyl portion, as representative variants include dimethylamino, diethylamino and the like for safening seeds, especially barley seeds.

Most preferred are the benzothiazoles selected from the group consisting of 4-difluoromethoxybenzo-1,2,3-thiadiazole, 5-cyanobenzo-1,2,3-thiadiazole, 6-methylbenzo-1,2,3-thiadiazole and 6-hydroxybenzo-1,2,3-thiadiazole.

Another preferred group of benzothiazoles are those compounds of formula I wherein X represents CH, and A is a nitro group attached to the 5-position of the benzothiazole moiety.

The benzothiazoles of formula I are known in the art and may be prepared by the processes described in U.S. Pat. Nos. 4,931,581, and 5,229,384, EP 0 039 795 and British Patent 1177972.

Herbicides which are suitable for use in the present invention include, but are not limited to, AHAS-inhibiting herbicides, ACCase-inhibiting herbicides and HPPD-inhibiting herbicides. Preferred herbicides of the present invention include imidazolinone herbicides such as methyl 6-(4-isopropyl-4-methyl-5-oxo-2-imidazolin-2-yl)-m-toluate and methyl 2-(4-isopropyl-4-methyl-5-oxo-2-imidazolin-2-yl)p-toluate (imazamethabenz-methyl), 5-ethyl-2-(4-isopropyl-4-methyl-5oxo-2-imidazolin-2-y) nicotinic acid (imazethapyr), 2-(4-isopropyl-4-methyl-5-oxo-2-imidazolin-2-y)nicotinic acid, 5-methoxymethyl-2-(4-isopropyl-4-methyl-5oxo-2-imidazolin-2-y)nicotinic acid and 2-(4-isopropyl-4-methyl-5-oxo-2-imidazolin-2-yl) quinoline-3-carboxylic acid (imazaquin); aryloxyphenoxy propionic acids, such as fenoxaprop including fenoxaprop-P and fenoxaprop-P-ethyl, and clodinafop including clodinafop-propargyl and a mixture of clodinafop-propargyl and cloquintocet; and benzothiopyran derivatives such as (E)-6-{{1-ethyl-5-[(propylsulfonyl)oxy]pyrazol-4-yl}carbonyl}-2,3-dihydro-5-methyl-4-oxo-1,1-dioxide-4H-1-benzothiopyran, 4-(O-methyloxime) and the zinc chelate of (E)-6-{{1-ethyl-5-hydroxypyrazol-4-yl}carbonyl}-2,3-dihydro-5-methyl-4-oxo-1,1-dioxide-4H-1-benzothiopyran, 4-(O-methyloxime).

Although many of these herbicides have been used with success in certain crops, they have been found to be phytotoxic in many cereal crops. Surprisingly, it has been found that by applying certain benzothiazole derivatives of formula I to the crop plant, the seed of the crop, or the soil surrounding the crop or crop seed, the herbicide is safened.

Safening of cereal crops such as corn, wheat, barley and rice from the post emergence application of herbicides may also be effected by allowing said crop plants to grow until the third to early fourth leaf stage and then spraying with an aqueous solution of the safener either alone, or tank-mixed with at least one of the above-described herbicides. The tank mix should contain effective amounts of herbicide and effective amounts of the safener. Although rates will naturally vary with the particular herbicide and crop, typical rates of application for the safener are about 0.05 kg/ha to 2.0 kg/ha.

The application rate of the compound of the herbicides is usually in the range of 0.001 to 2.0 kg/ha, with rates between 0.02–0.5 kg/ha often achieving satisfactory control. In general, the preferred application rate of the herbicides is in the range of 0.01 to 0.5 kg/ha, preferably 0.02–0.3 kg/ha.

The optimal rate for a specific application will depend on the crop(s) under cultivation and the predominant species of infesting weed species, and readily may be determined by established biological tests known to those skilled in the art.

A wide variety of troublesome weed species can also be effectively controlled in the presence of important agronomic crops such as corn, wheat, barley and rice by safening the crop plants by any conventional seed treatment techniques or uniformly coating the seeds with 0.01 to 0.5 % by weight of the safener.

The herbicides can be co-formulated together with the safener in a suitable ratio according to the present invention, together with usual carriers and/or additives known in the art.

Accordingly, the present invention further provides a herbicidal composition which comprises a carrier and, as active ingredient, at least one herbicide as defined above and at least one safener compound of formula I as defined above.

A method of making such a composition is also provided which comprises bringing the compound of formula I and the herbicidal active ingredient as defined above into association with at least one carrier. It is also envisaged that different isomers or mixtures of isomers of formula I and/or the herbcidal active ingredient may have different levels or spectra of activity and thus compositions may comprise individual isomers or mixtures of isomers.

A carrier in a composition according to the invention is any material with which the active ingredient is formulated to facilitate application to the locus to be treated, which maybe, for example, a plant, seed, foliage, soil, or into the water where the plant grows, or to the roots or to facilitate storage, transport or handling. A carrier may be a solid or a liquid, including material which is normally a gas but which has been compressed to form a liquid.

The compositions may be manufactured into a variety of formulations suitable for agricultural use, e.g. emulsion concentrates, solutions, oil in water emulsions, wettable powders, soluble powders, suspension concentrates, dusts, granules, water dispersible granules, tablets, micro-capsules, gels and other formulation types by well-established procedures. These procedures include intensive mixing and/or milling of the active ingredients with other substances, such as fillers, solvents, solid carriers, surface active compounds (surfactants), and optionally, solid and/or liquid auxilaries and/or adjuvants. The form of application, such as spraying, atomizing, dispersing or pouring may be chosen according to the desired objectives and the given circumstances.

The biological activity of the active ingredient can also be increased by including an adjuvant in the formulation or the spray dilution. An adjuvant is defined here as a substance which can increase the biological activity of an active ingredient but which, by itself, is not significantly biologically active. The adjuvant can either be included in the formulation as a coformulant or carrier, or can be added to the spray tank together with the formulation containing the active ingredient.

As a commodity, the compositions of the present invention are preferably in a concentrated form which is then diluted for use by the end user. The concentrated compositions are typically diluted to a concentration down to 0.001% of active ingredient for application to the target. The typical doses of the herbicide ingredient are usually in the range from 0.01 to 0.5 kg ha and of safener are usually in the range from 0.05 to 2.0 kg/ha.

In a preferred embodiment, the herbicide and the safener of formula I are added to the tank mix together each as individual formulations.

A preferred embodiment of the present invention thus relates to a kit for the preparation of a spray mixture consisting of two separate containers: (a) a container which comprises at least one safener of formula I, conventional carriers and optional adjuvants; and (b) a container which comprises at least one herbicidal active ingredient, preferably one or more compounds selected from the group consisting of methyl 6-(4-isopropyl-4-methyl-5-oxo-2-imidazolin-2-yl)-m-toluate, methyl 2-(4-isopropyl-4-methyl-5-oxo-2-imidazolin-2-yl)p-toluate, 5-ethyl-2-(4-isopropyl-4-methyl-5-oxo-2-imidazolin-2-yl)nicotinic acid, 5-methoxymethyl-2-(4-isopropyl-4methyl-5-oxo-2-imidazolin-2-yl)nicotinic acid, 2-(4-isopropyl-4-methyl-5-oxo-2-imidazolin-2-yl) quinoline-3-carboxylic acid; fenoxaprop; clodinafop; (E)-6-{{1-ethyl-5-[(propylsulfonyl)oxy]

pyrazol-4-yl}carbonyl}-2,3-dihydro-5-methyl-4-oxo-1,1-dioxide-4H-1-benzothiopyran, 4-(O-methyloxime) and the zinc chelate of (E)-6-{{1-ethyl-5-hydroxypyrazol-4-yl}carbonyl}-2,3-dihydro-5-methyl-4-oxo-1,1-dioxide-4H-1-benzothiopyran, 4-(O-methyloxime), conventional carriers and optional adjuvants.

In a preferred embodiment, the kit will consist of two bottles with dispensing means which allow the easy and correct addition of the active ingredients (a) and (b) to the tank mix.

The compositions of this invention can be applied to the plants or their environment simultaneously with, or in succession to, other active substances. These other active substances can be fertilizers, agents which donate trace elements, or other preparations which influence plant growth. However, they can also be other fungicides, selective herbicides, insecticides, bactericides, nematicides, algicides, molluscidides, rodenticides, virucides, compounds inducing resistance into plants, biological control agents, such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

The present invention is of wide applicability in the protection of crops, trees, residential and ornamental plants against attack by weed species. Preferred crops are cereals, such as corn, wheat and barley, rice, as well as vines and apples. The duration of the protection is normally dependent on the individual compound selected, and also a variety of external factors, such as climate, whose impact is normally mitigated by the use of a suitable formulation.

The following examples further illustrate the present invention. It should be understood, however, that the scope of the invention is not limited solely to the particular examples given below.

EXAMPLES

The following crops are included:

ZEAMX *Zea mays* corn Pioneer Hybrid 3514
HORVW *Hordeum vulgare* winter-barley cultivar "Mammut"
The following compounds of formula I are used:

| Compound No. | Formula |
| --- | --- |
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |

The following herbicides are used: p1 (E)-6-{{1-ethyl-5-[(propylsulfonyl)oxy]pyrazol-4-yl}carbonyl}-2,3-dihydro-5-methyl-4-oxo-,1-dioxide-4H-1-benzothiopyran, 4-(O-methyloxime) coded Benzothiopyran A,
  zinc chelate of (E)-6-{{1-ethyl-5-hydroxypyrazol-4-yl}carbonyl}-2,3-dihydro-5-methyl-4-oxo-1,1-dioxide-4H-1-benzothiopyran, 4-(O-methyloxime) coded Benzothiopyran B,
  5-methoxymethyl-2-(4-isopropyl4-methyl-5-oxo-2-imidazolin-2-yl)nicotinic acid coded Imidazoline A,
  2-(4-isopropyl-4-methyl-5-oxo-2-imidazolin-2-yl) nicotinic acid coded Imidazoline B,
  5-ethyl-2-(4-isopropyl-4-methyl-5-oxo-2-imidazolin-2-yl)nicotinic acid coded Imidazoline C,
  ethyl (R)-2-[4-chloro(6-benzoxazol-2-yloxy)-phenoxy]-propionate coded Fenoxaprop-P,
  prop-2-ynyl (R)2-[4-(5-chloro-3fluoro-2-pyridinyloxy) phenoxypropionate coded Clodinafop. Clodinafop is commercially used in admixture with 1-methylhexyl (5chloroquinolin-8-yloxy)-acetate (Cloquintocet) as a safener.

EXAMPLE 1
Benzothiazole Corn Seed Treatment as Safener for Benzothiopyran Herbicides Titrations of herbicides with untreated seed were used to determine a herbicide dose that would cause approximately 50% injury. Seed treatments were achieved by dissolving the test compounds in acetone at 1 mg/ml then treating six corn seeds at a dose of 1 mg of test compound per seed. The seed treatments were applied one day before planting. The seeds were then planted in cups containing artificial soil, and the cups were placed in aluminum pans. The herbicides were dissolved in 500 ml water. The plants in the aluminum pans were placed in a greenhouse, and the herbicide solutions were added to the aluminum pans. The plants absorbed the herbicides through the water solution taken up through the cups. Water was added to the pans daily throughout the tests. The results of the test were evaluated twelve days after planting and are shown in the following table I.

TABLE 1

| | Herbicide Treatment | | | |
|---|---|---|---|---|
| Seed treatment | Benzothiopyran A (5 ppm) | | Benzothiopyran B (6 ppm) | |
| Compound No. | % stunting | % bleaching | % stunting | % bleaching |
| acetone | 70 | 30 | 40 | 80 |
| 2 | 70 | 30 | 20 | 20 |
| 3 | 60 | 25 | 40 | 80 |
| 4 | 60 | 25 | 30 | 70 |
| 5 | 65 | 30 | 35 | 75 |
| 7 | 40 | 20 | 15 | 15 |
| 8 | 65 | 30 | 20 | 65 |
| 9 | 60 | 25 | 20 | 65 |

EXAMPLE 2
Benzothiazole Corn Seed Treatment as Safener for Imidazoline Herbicides The tests were conducted as described in Example 1 except for the herbicides used. The results of these tests were evaluated twelve days after planting and are shown in the following table II.

TABLE II

| | Herbicide Treatment | | |
|---|---|---|---|
| Seed treatment Compound No. | Imidazoline A (0.5 ppm) % stunting | Imidazoline B (0.75 ppm) % stunting | Imidazoline C (0.75 ppm) % stunting |
| acetone | 60 | 60 | 80 |
| 2 | 6o | 50 | 80 |
| 4 | 50 | 60 | 70 |
| 7 | 60 | 50 | 60 |

EXAMPLE 3
Benzothiazole Barley Seed Treatment as Safener for Clodinafop and Fenoxaprop-P For the seed treatments of barley, the required number of seeds for each treatment was counted into a small glass jar. The respective safener was dissolved in water (formulated material) or 80/20 acetoneAwater (technical material) at the concentration needed to give the desired loading of safener in g per kg seed. This solution was poured onto the seeds and the jar was shaken vigorously until all the seeds were bathed in the safener solution. The seeds were then poured onto a glass plate and left in the fume hood to dry. The dry seeds were planted into greenhouse soil (see below) and were treated with herbicides seven days after planting (post-emergence application).

Herbicide treatments were applied in water (formulated material) or in acetonic solution (technical material), respectively. This solution was prepared by dissolving the technical material at a concentration of 0.5% a.i. in acetone containing 0.5% of the adjuvant Triton X-100. The solution was topped up with water to give the final volume needed for the application and was applied with a pneumatic sprayer calibrated to deliver 400 l/ha spray volume.

All plants were grown in a mixture of field soil (sandy loam soil with 1.9% organic matter, pH=7.7) and compost 1/1.

Visual ratings of crop injury were taken 2 weeks after treatment (DAT) and were expressed using a 0–100% scale with 0 no effect and 100=total kill.

The results of these tests are shown in the following tables III to VIII.

TABLE III

| Treatment seeds | Herbicide Treatment Post-emergence | Dose g seeds | Dose g treatments | HORVW % crop injury |
|---|---|---|---|---|
| Control | | | | 0 |
| 1 | | 1 | | 0 |
| | | 0.1 | | 0 |
| | | 0.01 | | 0 |
| | Clodinafop | | 30 | 22 |
| 1 | Clodinafop | 1 | 30 | 17 |
| | Clodinafop | 0.1 | 30 | 10 |
| | Clodinafop | 0.01 | 30 | 2 |
| | Fenoxaprop-P | | 120 | 57 |
| 1 | Fenoxaprop-P | 1 | 120 | 40 |
| | Fenoxaprop-P | 0.1 | 120 | 37 |
| | Fenoxaprop-P | 0.01 | 120 | 17 |

TABLE IV

| Treatment seeds | Herbicide Treatment Post-emergence | Dose g seeds | Dose g treatments | HORVW % crop injury |
|---|---|---|---|---|
| Control | | | | 0 |
| 2 | | 1 | | 30 |
| | | 0.1 | | 12 |
| | | 0.01 | | 7 |
| | Fenoxaprop-P | | 120 | 57 |
| 2 | Fenoxaprop-P | 1 | 120 | 30 |
| | Fenoxaprop-P | 0.1 | 120 | 45 |
| | Fenoxaprop-P | 0.01 | 120 | 60 |

TABLE V

| Treatment seeds | Herbicide Treatment Post-emergence | Dose g seeds | Dose g treatments | HORVW % crop injury |
|---|---|---|---|---|
| Control | | | | 0 |
| 3 | | 1 | | 0 |
| | | 0.1 | | 0 |
| | | 0.01 | | 0 |
| | Clodinafop | | 60 | 47 |
| | Clodinafop | | 30 | 22 |
| 3 | Clodinafop | 1 | 60 | 32 |
| | Clodinafop | 0.01 | 60 | 36 |
| 3 | Clodinafop | 1 | 30 | 4 |
| | Clodinafop | 0.1 | 30 | 4 |
| | Clodinafop | 0.01 | 30 | 2 |

TABLE V-continued

| Treatment seeds | Herbicide Treatment Post-emergence | Dose g seeds | treatments | HORVW % crop injury |
|---|---|---|---|---|
|  | Clodinafop + Cloquintocet |  | 120 | 22 |
| 3 | Clodinafop + Cloquintocet | 1 | 120 | 2 |
|  | Clodinafop + Cloquintocet | 0.1 | 120 | 5 |
|  | Clodinafop + Cloquintocet | 0.01 | 120 | 6 |
|  | Fenoxaprop-P |  | 120 | 57 |
|  | Fenoxaprop-P |  | 60 | 12 |
| 3 | Fenoxaprop-P | 1 | 120 | 3 |
|  | Fenoxaprop-P | 0.1 | 120 | 10 |
|  | Fenoxaprop-P | 0.01 | 120 | 14 |
| 3 | Fenoxaprop-P | 1 | 60 | 1 |
|  | Fenoxaprop-P | 0.1 | 60 | 3 |
|  | Fenoxaprop-P | 0.01 | 60 | 3 |

TABLE VI

| Treatment seeds | Herbicide Treatment Post-emergence | Dose g seeds | treatments | HORVW % crop injury |
|---|---|---|---|---|
| Control |  |  |  | 0 |
| 4 |  | 1 |  | 0 |
|  |  | 0.1 |  | 0 |
|  |  | 0.01 |  | 0 |
|  | Clodinafop |  | 30 | 25 |
| 4 | Clodinafop | 1 | 30 | 25 |
|  | Clodinafop + Cloquintocet |  | 120 | 27 |
|  | Clodinafop + Cloquintocet |  | 60 | 20 |
| 4 | Clodinafop + Cloquintocet | 1 | 120 | 12 |
|  | Clodinafop + Cloquintocet | 0.1 | 120 | 20 |
|  | Clodinafop + Cloquintocet | 1 | 60 | 5 |
|  | Clodinafop + Cloquintocet | 0.1 | 60 | 1 |
|  | Clodinafop + Cloquintocet | 0.01 | 60 | 4 |
|  | Fenoxaprop-P |  | 120 | 55 |
|  | Fenoxaprop-P |  | 60 | 25 |
| 4 | Fenoxaprop-P | 1 | 120 | 5 |
|  | Fenoxaprop-P | 0.1 | 120 | 46 |
|  | Fenoxaprop-P | 1 | 60 | 2 |
|  | Fenoxaprop-P | 0.1 | 60 | 10 |

TABLE VII

| Treatment seeds | Herbicide Treatment Post-emergence | Dose g seeds | treatments | HORVW % crop injury |
|---|---|---|---|---|
| check |  |  |  | 0 |
| 5 |  | 1 |  | 0 |
|  |  | 0.1 |  | 0 |
|  |  | 0.01 |  | 0 |
|  | Clodinafop + Cloquintocet |  | 120 | 27 |
|  | Clodinafop + Cloquintocet |  | 60 | 20 |
| 5 | Clodinafop + Cloquintocet | 1 | 120 | 20 |
|  |  | 0.1 | 120 | 5 |
|  |  | 0.1 | 120 | 5 |
|  |  | 0.01 | 120 | 2 |
|  |  | 1 | 60 | 1 |
|  |  | 0.1 | 60 | 0 |
|  |  | 0.01 | 60 | 0 |
|  | Fenoxaprop-P |  | 60 | 25 |
| 5 | Fenoxaprop-P | 1 | 60 | 7 |
|  |  | 0.1 | 60 | 4 |
|  |  | 0.01 | 60 | 1 |

TABLE VIII

| Treatment seeds | Herbicide Treatment Post-emergence | Dose g seeds | treatments | HORVW % crop injury |
|---|---|---|---|---|
| check |  |  |  | 0 |
| 6 |  | 1 |  | 0 |
|  |  | 0.1 |  | 0 |
|  |  | 0.01 |  | 0 |
|  | Clodinafop |  | 60 | 50 |
|  |  |  | 30 | 25 |
| 6 | Clodinafop | 1 | 60 | 37 |
|  |  | 0.1 | 60 | 42 |
|  |  | 0.01 | 60 | 30 |
|  |  | 1 | 30 | 4 |
|  |  | 0.1 | 30 | 5 |
|  |  | 0.01 | 60 | 4 |
|  | Clodinafop + Cloquintocet |  | 120 | 27 |
|  |  |  | 60 | 20 |
| 6 | Clodinafop + Cloquintocet | 1 | 120 | 12 |
|  |  | 1 | 60 | 5 |
|  |  | 0.1 | 60 | 1 |
|  |  | 0.01 | 60 | 4 |
|  | Fenoxaprop-P |  | 120 | 55 |
|  |  |  | 60 | 25 |
| 6 | Fenoxaprop-P | 1 | 120 | 5 |
|  |  | 1 | 60 | 2 |
|  |  | 0.1 | 60 | 10 |

The benzothiazole derivatives displayed marked safening effects against crop injury from ACCase-inhibiting herbicides such as fenoxaprop-ethyl, clodinafop and the combination of clodinafop and cloquintocet. The benzothiadiazole No. 2 (BION), which controls powdery mildew in cereals by inducing systemic acquired resistance (SAR) in cereals, caused some inherent phytotoxicity in barley when used as a seed treatment. However, at the applied rate of 1 g/kg seed the SAR-compound No. 2 clearly reduced crop injury resulting from the post-emergence application of aryloxyphenoxy propionic acids such as fenoxaprop and clodinafop compared to plants grown from untreated seeds. None of the other benzothiadiazole derivatives used in the tests as a seed treatment caused crop injury in barley, and reduced crop damage of post-emergence treatments of aryloxyphenoxy propionic acids. In particular, Compounds No. 1 and No. 6 displayed marked safening effects to crop injury caused by either fenoxaprop P, clodinafop or the combination of clodinafop and cloquintocet.

What is claimed is:

1. A method for protecting cereal crops from injury caused by a herbicidally effective amount of a herbicide which comprises applying to the crop plant, the seed of the crop, or the soil surrounding the crop or crop seed a herbicidally effective amount of a herbicide and an effective non-phytotoxic antidotal amount of a benzothiazole derivative of formula I

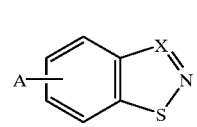

(I)

wherein

A represents an alkyl, alkoxy, haloalkoxy, hydroxy, cyano or nitro group or a group of the formula

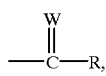

in which

W represents O or S, and

R represents a hydroxy, thiol, alkoxy, thioalkyl, amino, alkylamino or dialkylamino group; and X represents CH or N.

2. The method according to claim 1 wherein the herbicide is selected from the group consisting of AHAS-inhibiting, ACCase-inhibiting and HPPD-inhibiting herbicides.

3. The method according to claim 2 wherein the herbicide is an imidazolinone herbicide.

4. The method according to claim 3, wherein the herbicide is selected from the group consisting of an isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)p-toluate, 5-ethyl-2-(4-isopropyl-4-methyl-5oxo-2-imidazolin-2-yl)nicotinic acid, 2-(4-isopropyl-4-methyl-5oxo-2-imidazolin-2-yl)nicotinic acid, 5-methoxymethyl-2-(4-isopropyl-4-methyl-5oxo-2-imidazolin-2-yl)nicotinic acid and 2-(4-isopropyl-4-methyl-5-oxo-2-imidazolin-2-yl) quinoline-3-carboxylic acid.

5. The method according to claim 2 wherein the herbicide is an aryloxyphenoxy propionic acid or ester thereof.

6. The method according to claim 5 wherein the herbicide is selected from fenoxaprop, fenoxaprop-P, fenoxaprop-P-ethyl, clodinafop and clodinafop-propargyl.

7. The method according to claim 2 wherein the herbicide is an benzothiopyran derivative.

8. The method according to claim 7 wherein the herbicide is selected from (E)-6-{{1-ethyl-5-[(propylsulfonyl)oxy]pyrazol-4-yl}carbonyl}-2,3-dihydro-5-methyl-4-oxo-1,1-dioxide-4H-1-benzothiopyran, 4-(O-methyloxime) and the zinc chelate of (E)-6-{{1ethyl-5-hydroxypyrazol-4-yl}carbonyl}-2,3-dihydro-5-methyl-4-oxo-1,1-dioxide-4H-1-benzothiopyran, 4-(O-methyloxime).

9. The method according to claim 1, wherein X represents N, and A is a —CO—SCH$_3$ group attached to the 7-position of the benzothiadiazole moiety.

10. The method according to claim 1, wherein X represents N, and A is a methyl, cyano, hydroxy or difluoromethoxy group attached to the 4-, 5- or 6-position of the benzothiadiazole moiety.

11. The method according to claim 10, wherein the benzothiazole is selected from the group consisting of 4-difluoromethoxybenzo-1,2,3-thiadiazole, 5-cyanobenzo-1,2,3-thiadiazole, 6-methylbenzo-1,2,3-thiadiazole and 6-hydroxybenzo-1,2,3-thiadiazole.

12. The method according to claim 1, wherein X represents CH, and A is a nitro group attached to the 5-position of the benzothiazole moiety.

13. The method according to claim 1, wherein the crop or seed is wheat, barley, rice or corn.

14. The method according to claim 1, wherein the benzothiazole derivative of formula I is applied to the foliage of the crop.

15. The method according to claim 1, wherein the crop is corn and the benzothiazole derivative of formula I is applied to the corn seed.

16. The method according to claim 1, wherein the crop is corn and the herbicide is selected from 5-ethyl-2-(4-isopropyl-4-methyl-5-oxo-2-imidazolin-2-yl)nicotinic acid, 2-(4-isopropyl-4-methyl-5-oxo-2-imidazolin-2-y-1) nicotinic acid and 5-methoxymethyl-2-(4-isopropyl-4-methyl-5oxo-2-imidazolin-2-yl)nicotinic acid.

17. The method according to claim 1, wherein the crop is barley and the herbicide is fenoxaprop, fenoxaprop-P, fenoxaprop-P-ethyl, clodinafop or clodinafop-propargyl.

18. A crop seed treated with an effective nonphytotoxic antidotal amount of a benzothiazole derivative of formula I

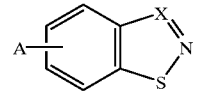

(I)

wherein

A represents an alkyl, alkoxy, haloalkoxy, hydroxy, cyano or nitro group or

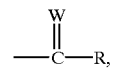

a group of the formula in which

W represents O or S, and

R represents a hydroxy, thiol, alkoxy, thioalkyl, amino, alkylamino or dialkylamino group; and X represents CH or N.

19. Barley seeds treated with an effective nonphytotoxic antidotal amount a benzothiadiazole derivative of formula I wherein A represents a methyl, hydroxy or a C$_{1-6}$ fluoroalkoxy group.

20. A safened herbicidal composition comprising a herbicidally effective amount of a herbicide and an effective nonphytotoxic antidotal amount a benzothiazole derivative of formula I

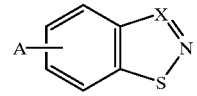

(I)

wherein

A represents an alkyl, alkoxy, haloalkoxy, hydroxy, cyano or nitro group or a group of the formula

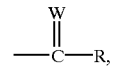

in which

W represents O or S, and

R represents a hydroxy, thiol, alkoxy, thioalkyl, amino, alkylamino or dialkylamino group; and X represents CH or N.

21. A safened herbicidal composition according to claim 20 comprising a herbicidally effective amount of a herbicide selected from the group consisting of AHAS-inhibiting, ACCase-inhibiting and HPPD-inhibiting herbicides.

* * * * *